United States Patent
Ko et al.

(10) Patent No.: US 9,012,614 B2
(45) Date of Patent: Apr. 21, 2015

(54) RAPID NUCLEIC ACID PURIFICATION USING PAPER CHROMATOGRAPHY

(75) Inventors: Minsu Ko, Yuseong-gu (KR); Young Cheol Kim, Yuseong-gu (KR); Siseok Lee, Yuseong-gu (KR)

(73) Assignee: Nanohelix Co., Ltd., Daejeon (KR)

( * ) Notice: Subject to any disclaimer, the term of this patent is extended or adjusted under 35 U.S.C. 154(b) by 135 days.

(21) Appl. No.: 13/698,112

(22) PCT Filed: Dec. 27, 2011

(86) PCT No.: PCT/KR2011/010158
§ 371 (c)(1),
(2), (4) Date: Jan. 10, 2013

(87) PCT Pub. No.: WO2012/157831
PCT Pub. Date: Nov. 22, 2012

(65) Prior Publication Data
US 2013/0137107 A1    May 30, 2013

(51) Int. Cl.
| | | |
|---|---|---|
| *C07H 21/00* | (2006.01) |
| *C12N 15/10* | (2006.01) |
| *C12Q 1/68* | (2006.01) |
| *G01N 30/90* | (2006.01) |
| *G01N 30/88* | (2006.01) |

(52) U.S. Cl.
CPC .......... *C12N 15/101* (2013.01); *C12N 15/1003* (2013.01); *C07H 21/00* (2013.01); *G01N 30/90* (2013.01); *G01N 2030/8827* (2013.01); *C12Q 1/6806* (2013.01); *C12Q 2523/308* (2013.01); *C12Q 2527/125* (2013.01); *C12Q 2531/113* (2013.01); *C12Q 2565/137* (2013.01)

(58) Field of Classification Search
None
See application file for complete search history.

(56) References Cited

U.S. PATENT DOCUMENTS

2008/0026451 A1 *   1/2008  Braman et al. ................ 435/270

OTHER PUBLICATIONS

Gorbulev et al., "The Separation of Oligonucleotides of Baker's-Yeast Valine Transfer Ribonucleic Acid 2b by High-Voltage Electrophoresis on DEAE-Paper and by Thin-Layer Chromatography," Biochem J., 1977, vol. 163, No. 3, pp. 409-410.
Rollin D. Hotchkiss, "The Quantitative Separation of Purines, Pyrimidines and Nucleosides by Paper Chromatography," Journal of Biochemistry, 1948, pp. 315-332.
Davidson et al., "The Separation by Ionophoresis on Paper of the Constituent Nucleotides of Ribonucleic Acid," Department of Biochemistry, University of Glasgow, 1952, vol. 52, pp. 594-599, Biochem J.
Southern et al., Chromatography of Nucleic Acid Digests on Thin Layers of Cellulose Impregnated with Polyethyleneimine, Biochem. J., 1971, vol. 123, pp. 613-617.

* cited by examiner

*Primary Examiner* — Samuel Woolwine
*Assistant Examiner* — Danna Bicknell
(74) *Attorney, Agent, or Firm* — Sughrue Mion, PLLC (57) ABSTRACT

Provided is a method for rapid nucleic acid purification. The method includes allowing the nucleic acid isolated from the biological sample to be adsorbed on a silica membrane; separating contaminants from the nucleic acid-adsorbed silica membrane by using paper chromatography; and eluting only high-purity nucleic acid from the silica membrane from which the contaminants are isolated by using a buffer, or applying at least one selected from direct PCR, RT-PCR, real-time PCR, and real-time RT-PCR to the nucleic acid bound onto the silica membrane.

3 Claims, 6 Drawing Sheets

FIG. 7

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Forward primer

<400> SEQUENCE: 1
gggatgatag tctgactttc ctaacct                                        27

<210> SEQ ID NO 2
<211> LENGTH: 25
<212> TYPE: DNA
<213> ORGANISM: Artificial Sequence
<220> FEATURE:
<223> OTHER INFORMATION: Reverse primer

<400> SEQUENCE: 2
gccttcagtc atgcctaggc ctgca                                          25

<210> SEQ ID NO 3
<211> LENGTH: 20
<212> TYPE: DNA
<213> ORGANISM: Artificial Sequence
<220> FEATURE:
<223> OTHER INFORMATION: Forward primer

<400> SEQUENCE: 3
caaggtgaac gtggatgaag                                                20

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
ggcagaatcc agatgctcaa                                                20

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
caaggtgaac gtggatgaag                                                20
```

```
<210> SEQ ID NO 6
<211> LENGTH: 21
<212> TYPE: DNA
<213> ORGANISM: Artificial Sequence
<220> FEATURE:
<223> OTHER INFORMATION: Reverse primer

<400> SEQUENCE: 6
attagccaca ccagccacca c                                              21
```

RAPID NUCLEIC ACID PURIFICATION USING PAPER CHROMATOGRAPHY

CROSS-REFERENCE TO RELATED APPLICATIONS

This application claims priority under 35 U.S.C. §119 to Korean Patent Application No. 10-2011-0045956, filed on May 16, 2011, in the Korean Intellectual Property Office, the disclosure of which is incorporated herein by reference in its entirety.

SEQUENCE LISTING

The instant application contains a Sequence Listing which has been submitted in ASCII format via EFS-Web and is hereby incorporated by reference in its entirety.

TECHNICAL FIELD

The following disclosure relates to a method for rapid nucleic acid purification, and more particularly, a method for rapid nucleic acid purification using a silica membrane and a buffer containing chaotropic salt and sarcosinate.

BACKGROUND

In order to purify nucleic acid from a sample containing the nucleic acid, physical and/or chemical purification processes need to be carried out. In most cases, it is general to remove a large-sized solid component from a liquid in the process of purifying the nucleic acid.

In particular, in the case where the nucleic acid is obtained by dissolving a biological sample, it is necessary to remove impurities including various kinds of protein components contained in a cell. In general, the impurities are removed by a precipitation method using centrifugation or by a filtering method with a filter. The former is frequently used in a laboratory, but is not appropriate in treating a large amount of samples and difficult to automate. Whereas, the latter is appropriate in continuously treating a large amount of samples by being applied to an automated device with a pressure reducing or applying device.

Chromosomal DNA needs to be isolated in the process of extracting only plasmid from Escherichia coil or bacterial transformants since an undesired reaction due to the chromosomal DNA needs to be prevented to progress during a gene amplification process, a gene sequencing process, a gene recombination process, or the like.

A method of separating nucleic acid from a tissue sample is largely divided into two steps. As the first step, tissue cells are lysed to thereby release all the cell components including all nucleic acids. This cell lysis procedure may be conducted by a physical or chemical method. However, the chemical method is widely used in order to minimize damage of the nucleic acid and effectively lyse tissue cells to thereby isolate the nucleic acid. In particular, an anionic surfactant such as sodium dodecyl sulfate (SDS) is mainly used.

As the second step, impurities are removed from the cell lysate to isolate pure nucleic acid. This method of extracting the nucleic acid uses treatment of an organic solvent such as phenol-chloroform, salting out, a chaotropic salt, and the like.

The method of separating nucleic acid from tissue cells through the above two steps is widely used, and thus, according to the existing methods of isolating nucleic acid, a cell lysis buffer containing a surfactant is used as a first buffer for extracting nucleic acid in order to facilitate isolation of nucleic acid from tissue cells. A second buffer in the process of separating nucleic acid is a buffer containing a high-concentration salt such as a chaotropic salt. The buffer containing this high-concentration salt has a very important role in removing impurities from the nucleic acid by salting out.

In order to isolate high-purity nucleic acid, the two kinds of buffers as described above are applied step by step to the tissue cells to thereby be used to remove impurities through cell lysis and salting out. Particularly, a cell lysate lysed in the cell lysis buffer containing sodium dodecyl sulfate is mixed with a buffer containing a high-concentration salt, followed by salting out, so that precipitation of impurities can be facilitated, and thus, this is very important in separating high-purity nucleic acid, and most widely used as a cell lysis buffer for effective cell lysis in the existing method of isolating nucleic acid.

Recently known nucleic acid isolation techniques are used in isolating the nucleic acid from the cell lysate by using a silica membrane or ion exchange chromatography. Particularly, according to the current widely used method, nucleic acid is isolated from the other impurities by being bound on a silica membrane, and the bound nucleic acid is obtained through washing and elution [Process for isolating nucleic acid (U.S. Pat. No. 5,234,809)].

However, in this method, the nucleic acid may be isolated from the impurities by being bound on the silica membrane, but a centrifugation step is necessary in all the steps of isolating the nucleic acid, and thus, the nucleic acid isolation procedure is difficult and needs to be performed only at a laboratory.

Moreover, when the two kinds of buffers as described above are mixed, they are severely crystallized, and thus may not be used in a mixture type, and the cell lysate lysed using this type of buffers may not be applied to a silica membrane, and thus, is not very appropriate as a high-speed nucleic acid solution.

Meanwhile, according to the nucleic acid isolation technique using the ion exchange chromatography, negatively charged nucleic acid is combined with a cation exchange resin and then isolated from impurities. This method necessarily requires isolation of nucleic acid using centrifugal separation, and is not appropriate in isolating nucleic acid for point-of-care testing (POCT) due to the need of a skilled person and complicated steps.

Also, in a case of a method of binding nucleic acid contained in a sample to magnetic particles combined with a carboxyl group and then isolating the nucleic acid from impurities, a large amount of samples need to be used, and this method is not appropriate in isolating nucleic acid for point-of-care testing (POCT) due to a complicated separation step of using the magnetic particles and a complicated nucleic acid separation step of separating the magnetic particles combined with the nucleic acid using centrifugation or magnet.

SUMMARY

The present inventors put in a great deal of effort to efficiently isolate nucleic acid from a biological sample containing the nucleic acid, and as the result, found that a buffer containing chaotropic salt and sarcosinate enhances adsorptive power of nucleic acid on a silica membrane, the nucleic acid being lysed and eluted from cells, to thereby rapidly and conveniently isolate high-purity nucleic acid in the blood and tissue sample, and then completed the present invention.

An embodiment of the present invention is to provide a method for high-speed nucleic acid isolation for rapid diagnosis such as point-of-care testing (POCT), by isolating nucleic acid from a small amount of sample even without using special equipment more rapidly and conveniently than the existing nucleic acid isolation method, to thereby simplify a nucleic acid isolation procedure.

In order to achieve the above object, the present invention provides a method for high-speed nucleic acid purification, capable of isolating high-purity nucleic acid from a biological sample by using paper chromatography.

The method for high-speed nucleic acid purification according to the present invention is characterized by including: spotting a cell lysate, which contains nucleic acid in a sample, on a silica membrane, and then performing, step by step, adsorption of the nucleic acid from the spotted cell lysate on the silica membrane, separation of contaminants by a liquid mobile phase buffer, and purification of the nucleic acid.

In the method for high-speed nucleic acid purification according to the present invention, a sequential three-buffer system is used. More specifically, the silica membrane is immersed in a cell lysate containing guanidine thiocyanate and sodium lauryl sarcosinate as main components, a mobile phase buffer containing guanidine thiocyanate as a main component, and an alcohol-based nucleic acid washing buffer, sequentially, so that only high-purity nucleic acid is purified.

In the method for high-speed nucleic acid purification according to the present invention, the nucleic acid bound on the silica membrane, which are obtained by the above method, is directly used in a polymerase chain reaction (PCR), so that the present invention can be efficiently used in point-of-care testing (POCT).

Hereinafter, the present invention will be described in detail.

The present invention provides a method for high-speed nucleic acid purification, where high-purity nucleic acid is isolated from a biological sample by using paper chromatography, the method comprising:

1) allowing the nucleic acid isolated from the biological sample to be adsorbed on a silica membrane;
2) separating contaminants from the nucleic acid-adsorbed silica membrane by using paper chromatography; and
3) eluting only high-purity nucleic acid from the silica membrane from which the contaminants are separated by using a buffer solution or applying at least one selected from direct PCR, RT-PCR, real-time PCR, and real-time RT-PCR to the nucleic acid bound onto the silica membrane.

In the present invention, the stage 1) is characterized by allowing the nucleic acid extracted from cells lysed by a cell lysis buffer to be adsorbed on the silica membrane using paper chromatography.

As the biological sample of the present invention, a non-coagulating blood sample treated with a small amount of Na-EDTA or heparin or a tissue sample may be used. Since the nucleic acid is well bound onto the silica membrane, impurities can be removed from the nucleic acid by the mobile phase buffer according to the present invention even without special equipment, to thereby isolate high-purity nucleic acid at a high speed.

In the present invention, the cell lysis buffer effectively lyses the tissue cells and extracts DNA from the lysed cells. The cell lysis buffer contains guanidine thiocyanate and sodium lauryl sarcosinate as main components. A buffer for isolating RNA may further include an anti-oxidant chemical material, and more particularly 2-mercaptoethanol or dithiothreitol.

In the present invention, the stage 2) is characterized in that the nucleic acid-adsorbed silica membrane is subjected to first development through developing using a mobile phase buffer, to thereby separate the contaminants, and the mobile phase buffer contains guanidine thiocyanate as a main component.

In the present invention, the stage 3) performed after the stage 2) is characterized in that the silica membrane from which the contaminants of the stage 2) are separated is subjected to second development using a nucleic acid washing buffer, to thereby remove high-concentration salt contained in the cell lysis buffer and the mobile phase buffer of the stage 2), so that high-purity nucleic acid can be purified.

More specifically, in order to obtain high-purity nucleic acid, it is necessary to effectively extract the nucleic acid from the tissue cells, allow the nucleic acid to be efficiently bound onto the silica membrane, effectively remove impurities mixed with the nucleic acid, and perform washing for increasing purity of the nucleic acid.

The method according to the present invention is characterized in that the nucleic acid adsorbed on the silica membrane is isolated by paper chromatography using a silica membrane, to thereby obtain high-purity nucleic acid, and through stepwise paper chromatographic development, adsorption of the nucleic acid on the silica membrane by a liquid mobile phase buffer, separation of the contaminants, and purification of the nucleic acid may occurs step by step.

More specifically, in order to isolate, step by step, high-purity nucleic acid from the biological sample through a sequential three-buffer system used in the present invention, as the first step, the tissue cells are effectively lysed by using a cell lysis buffer, and the nucleic acid is efficiently eluted therefrom, to thereby allow the nucleic acid to be bound onto the silica membrane. The cell lysis buffer contains sodium lauryl sarcosinate, and thus effectively lyses the tissue cells to thereby facilitate isolation of the nucleic acid. Also, the cell lysis buffer contains high-concentration guanidine thiocyanate, and thus, allows the extracted nucleic acid to be effectively bound onto the silica membrane.

As the second step, by using a mobile phase buffer containing high-concentration guanidine thiocyanate, water-soluble proteins and other impurities can be effectively removed from the nucleic acid bound onto the silica membrane by chromatography using the mobile phase, and also, the binding force of the nucleic acid onto the silica membrane can be enhanced. As the mobile phase buffer, a nucleic acid binding buffer containing high-concentration guanidine thiocyanate may be used.

Finally, in order to increase purity of the nucleic acid and remove lipid-based impurities, an ethanol-based nucleic acid washing buffer was used as a mobile phase.

In the specific examples of the present invention, the nucleic acid is isolated from the blood by using paper chromatography and the existing spin column method using centrifugation, respectively and then, the amplification ability of a target gene was confirmed by using RT-PCR and real-time RT-PCR, respectively.

As the result, it can be confirmed that the nucleic acid can be conveniently and rapidly isolated from a small amount of sample even without using special equipment, in the present invention, as compared with the nucleic acid isolation method of the related art.

DETAILED DESCRIPTION OF EMBODIMENTS

The present invention will be described in more detail with reference to the following examples. However, the following examples are provided only for assisting in the entire understanding of the present invention, and do not intend to limit the scope of the present invention.

Here, unless indicated otherwise, the terms used in the specification including technical and scientific terms have the same meaning as those that are usually understood by those who skilled in the art to which the present invention pertains, and detailed description of the known functions and constitutions that may obscure the gist of the present invention will be omitted.

EXAMPLE 1

Verification on Whether or not Nucleic Acid is Isolated Using Silica Membrane

Nucleic acid was extracted from a non-coagulating blood sample by using a cell lysis buffer, and then it was tested whether or not the nucleic acid may be bound onto or isolated from a silica membrane.

As a material for isolation of nucleic acid, a non-coagulating blood sample treated with a small amount of Na-EDTA or heparin was used. 25 μl or 50 μl of a blood sample was added and mixed into 500 μl of each of three kinds of cell lysis buffers (A, B, and C) having component ratios different from one another as shown in Table 1 below, and then, strongly vortexed by applying physical force thereto. Then, isopropanol (2-propanol) was mixed into each of the cell lysates at a volume ratio of 0.6 volumes based on the cell lysate, and then a silica membrane (0.5 cm wide×0.5 cm long) was immersed in the cell lysate.

TABLE 1

| | Cell Lysis Buffer | | |
|---|---|---|---|
| Component | Buffer A (pH 7.0) | Buffer B (pH 8.0) | Buffer C (pH 8.0) |
| Tris-HCl | 10 mM | 10 mM | 5 mM |
| EDTA | 5 mM | 5 mM | 2.5 mM |

TABLE 1-continued

| | Cell Lysis Buffer | | |
|---|---|---|---|
| Component | Buffer A (pH 7.0) | Buffer B (pH 8.0) | Buffer C (pH 8.0) |
| Guanidine thiocyanate | 3M | 3M | 0.8M |
| sodium citrate | — | — | 12 mM |
| sodium lauryl sarcosinate | 0.5% | 0.5% | 0.5% |
| Proteinase K | 160 ug | 160 ug | 160 ug |

After that, the silica membrane was washed with 80% of ethyl alcohol, followed by drying, and the nucleic acid bound onto the silica membrane was eluted in a tube containing 100 μl of a TE buffer (10 mM Tris-Cl, pH 8.0, 1 mM EDTA). In order to verify whether or not the nucleic acid is isolated and the amount of nucleic acid isolated, the nucleic acid was extracted from the remaining cell lysate by in the existing spin column method using centrifugal separation, and the comparison and analysis results thereof were tabulated in Table 2. The analysis was carried out by quantifying the wavelength absorption value of the isolated DNA using a NANODROP™ UV-Spectrophotometer at 260 nm, and the results thereof were tabulated in Table 2.

TABLE 2

| Amount of DNA isolated by using silica membrane | | | | | | | | | | | |
|---|---|---|---|---|---|---|---|---|---|---|---|
| Spin column elution | | | | | | Membrane elution | | | | | |
| Blood vol (μl) | | | | | | | | | | | |
| 50 | | | 25 | | | 50 | | | 25 | | |
| μg/μl elute | | | | | | | | | | | |
| 0.2 | 0.5 | 0.3 | 0.4 | 0.8 | 0.7 | 2.7 | 1.3 | 1.1 | 0.7 | 1.8 | 0.4 |
| A | B | C | A | B | C | A | B | C | A | B | C |

(bottom row: Cell lysis buffer)

As the result, Table 2 confirmed that the nucleic acid eluted from the cell lysis buffer was well bound onto and isolated from the silica membrane, and moreover, this method allowed a larger amount of nucleic acid to be extracted as compared with the existing spin column method using centrifugal separation.

EXAMPLE 2

Rapid DNA Isolation by Employing Paper Chromatography

Rapid DNA Isolation

The experiment of Example 1 confirmed that the nucleic acid extracted from the non-coagulating blood sample was well bound onto and isolated from the silica membrane. When DNA-based nucleic acid is isolated by using the three kinds of cell lysis buffers, extraction of nucleic acid, and elution of nucleic acid by adsorption on the silica membrane, are possible in all the buffers regardless of whether or not sodium citrate is contained in the buffers, and thus, Buffer A with pH 7.0 was selected from the three kinds of cell lysis buffers tested. Based on the above results, it was tested whether or not the nucleic acid was isolated by employing paper chromatography for rapid nucleic acid isolation and whether or not a target DNA was PCR-amplified.

In general, an impurity removing procedure is very important in order to isolate nucleic acid from tissue cells. In particular, it is very important to remove protein-based impurities generated due to lysis of the tissue cells in separating high-purity nucleic acid. To achieve this, among many methods for nucleic acid isolation, protease is applied in a buffer for separating nucleic acid in order to effectively remove protein. Although the application of the protease is effective in removing the protein-based impurities, high-concentration nucleic acid can be isolated from a special tissue sample such as a blood sample, even without using this enzyme. Therefore, in buffer B confirmed in Example 2, it was tested whether or not the nucleic acid is isolated through paper chromatography, by using a cell lysis buffer (A-1) applying Proteinase K, which is protease, and a cell lysis buffer (A-2) not applying Proteinase K.

To achieve this, 5 μl of a non-coagulating blood sample was added in each of the tubes respectively containing 25 μl of cell lysis buffers A-1 and A-2 having the component ratios of Table 3 below, followed by mixing, and then, strongly vortexed by applying physical force thereto. Then, isopropanol was added and mixed into each of the cell lysates at a volume ratio of 0.6 based on the cell lysate, to thereby prepare each cell lysate.

TABLE 3

| Cell Lysis Buffer | | |
|---|---|---|
| Component | Buffer A-1 | Buffer A-2 |
| Tris-HCl | 10 mM (pH 7.0) | 10 mM (pH 7.0) |
| EDTA | 5 mM | 5 mM |
| Guanidine thiocyanate | 3M | 3M |
| Sodium lauryl sarcosinate | 0.5% | 0.5% |
| Proteinase K | 160 ug | — |

Figure 1:
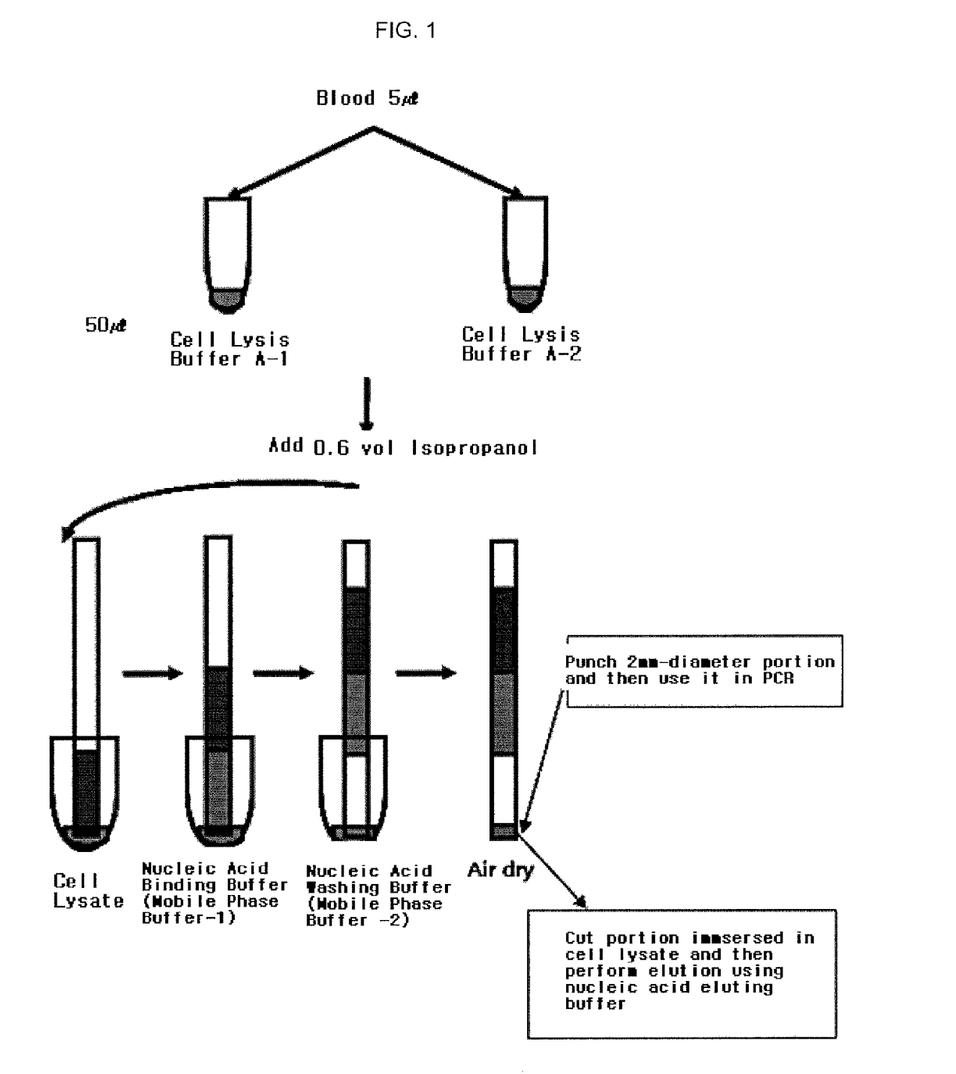
FIG. 1 is a comparison diagram of a method for rapid DNA isolation according to whether or not proteinase K is added in a cell lysis buffer.

The isolation of nucleic acid was tested by the method represented in FIG. 1, in order to isolate the nucleic acid by allowing the nucleic acid eluted in the cell lysate to be bound onto the silica membrane and removing impurities through the development of a mobile phase solution by paper chromatography. To achieve this, a silica membrane (0.5 cm wide and 10 cm long) was immersed approximately up to 0.5 cm from a bottom edge thereof in the cell lysate, and the eluted nucleic acid was bound onto the silica membrane. An end portion of the silica membrane, which has been immersed in the cell lysate, was immersed in a tube containing a 100 μl of nucleic acid binding buffer having a component ratio of Table 4 below, which is a first mobile phase buffer. After that, impurities were separated and then removed by a mobile phase solution through paper chromatography while the nucleic acid bound onto the silica membrane was intactly maintained.

TABLE 4

| Nucleic acid binding buffer (mobile phase buffer -1) | |
|---|---|
| Component | Nucleic acid binding buffer |
| Tris-HCl | 5 mM |
| EDTA | 2.5 mM |
| Guanidine thiocyanate | 1.5M |
| sodium lauryl sarcosinate | 0.25% |
| isopropanol | 40% |

Then, the end portion of the silica membrane was immersed in a tube containing 400 μl of a nucleic acid washing buffer (80% ethanol), which is a second mobile phase buffer, and then impurities were further removed and the nucleic acid was washed. Then, a 2 mm-diameter piece was separated from the portion of the silica membrane, which has been immersed in the cell lysate, by punching, and then PCR detection test for a target DNA was conducted. The remaining portion of the silica membrane was immersed in 100 μl of a TE buffer, which is a DNA eluting buffer, to thereby melt out DNA, and the isolated DNA was quantified by using a NANO-DROP™ UV-Spectrophotometer, and the results thereof were tabulated in Table 5.

TABLE 5

| Amount of DNA isolated by using silica membrane according to the use or nonuse of Proteinase K | | | | | |
|---|---|---|---|---|---|
| Cell Lysis Buffer A-1 (+Pro K) | | | Cell Lysis Buffer A-2 (−Pro K) | | |
| μg/μl elute | | | | | |
| 2 | 1 | 0.7 | 1.5 | 1 | 0.6 |
| Repeat No. of experiment | | | | | |
| 1 | 2 | 3 | 1 | 2 | 3 |

As the result, it can be confirmed from Table 5, that the nucleic acid was efficiently extracted by the two kinds of cell lysis buffers A-1 and A-2 regardless of whether or not proteinase K, which is protease, is applied. This results show that, in a method for rapid nucleic acid isolation using paper chromatography, a protease treatment procedure may be applied depending on the tissue sample used in isolating the nucleic acid.

(2) PCR Detection of Target DNA from DNA

It was confirmed whether or not the target DNA is detectable from the DNA isolated while being bound onto the silica membrane by the method (1) of Example 2, through PCR.

To achieve this, a 2 mm-diameter portion was taken from a DNA-bound portion of the silica membrane, which has been isolated by paper chromatography, and then the PCR detection reaction thereof was performed by using a primer set designed from a beta-globin gene region on a human chromosomal DNA sequence, each 10 pmoles of a forward primer 5'-GGGATGATAGTCTGACTTTCCTAACCT-3' (SEQ ID NO: 1) and a reverse primer 5'-GCCTTCAGTCATGC-CTAGGCCTGCA-3' (SEQ ID NO: 2); and a reaction buffer containing 1 1.25 units of HELIXAMP™ Taq DNA polymerase, a final concentration 2.5 mM of $MgCl_2$, and 0.25 mM of dNTP mix. The PCR was performed in 50 μl of reaction volume under the conditions of 95° C, 20 seconds / 68° C, 1 minute (35 cycles). After the PCR, 10 μl of PCR products were analyzed on 1% of agaros gel through electrophoresis.

Figure 2:
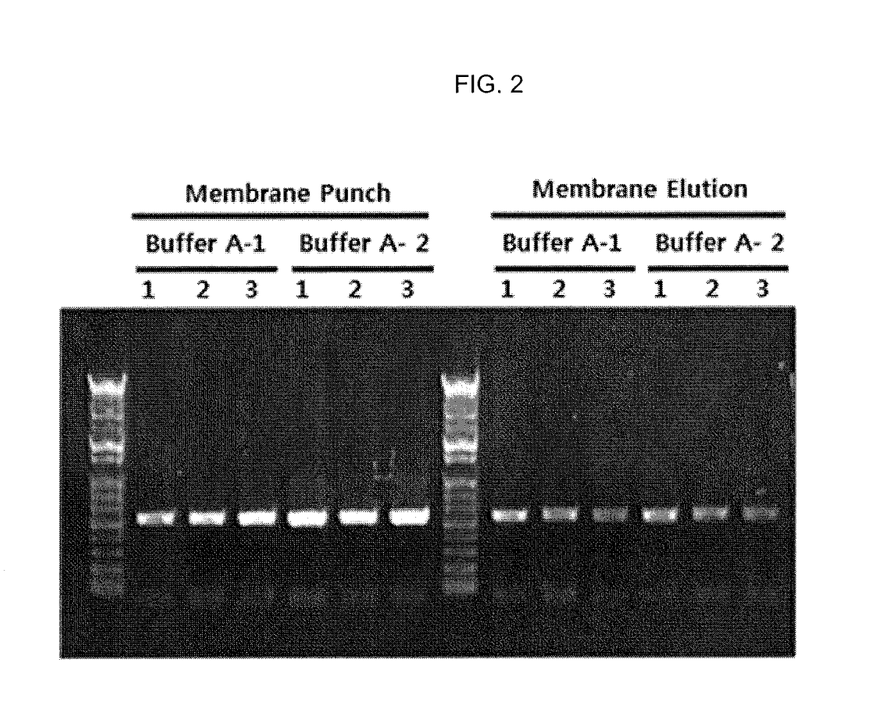
FIG. 2 shows PCR analysis results on a target gene from DNA isolated by the method for rapid nucleic acid purification, which is confirmed in FIG. 3.

As shown in FIG. 2, as the result of PCR, a target 550 bp-sized beta globin DNA portion was detected from the DNA-bounded silica membrane, and thus, it can be confirmed that the nucleic acid purification method of Example 2 allows high-purity nucleic acid to be promptly and conveniently isolated from the biological sample, and this method can be used in analysis of various nucleic acids using PCR.

EXAMPLE 3

Isolation of all Nucleic Acids from Blood Sample by Using Paper Chromatography

Isolation of all Nucleic Acids from Blood Sample

Diagnosis and molecular detection of causes of disease may be performed from RNA as well as DNA of the causes of disease. This fact is very important in almost molecular diagnoses. Hence, all the nucleic acids including both DNA and RNA isolated by Example 2 were tested, and RT-PCR detection of a target RNA from the all the isolated nucleic acids was tested. In general, in the procedure of separating nucleic acid from the tissue sample, particularly in the procedure of isolating RNA, degradation of RNA due to RNase contamination leads to difficult detection of RNA, which may cause more severe problems in molecular diagonostic POCT. In order to prevent contamination of RNase and effectively isolate DNA and RNA in this nucleic acid isolation procedure, antioxidant chemicals such as 2-mercaptoethanol and dithiothreitol are used. These chemicals break disulfide bonds in the RNase molecule to thereby inactivate the RNA decomposing ability.

In the present example, in order to achieve rapid nucleic acid isolation by applying paper chromatography to all of the nucleic acids including DNA and RNA, it was tested whether or not all the nucleic acids including DNA and RNA are isolated by applying 2-mercaptoethanol as an antioxidant chemical to the cell lysis buffer A-2 of (1) of Example 2. In order to verify isolation of all of the nucleic acids through paper chromatography, it was confirmed whether or not both of DNA and RNA are isolated from the blood by the existing spin column manner nucleic acid isolation method using centrifugal separation, while using the cell lysis buffer A-2 (Buffer A-2) represented in (1) of Example 2 and a cell lysis buffer (Modified Buffer A-2) modified by applying 2-mercaptoethanol thereto, which are shown in Table 6 below.

TABLE 6

| Cell Lysis Buffer for isolation of all nucleic acids | | |
|---|---|---|
| Component | Buffer A-2 | Modified Buffer A-2 |
| Tris-HCl | 10 mM (pH 7.0) | 10 mM (pH 7.0) |
| EDTA | 5 mM | 5 mM |
| Guanidine thiocyanate | 3M | 3M |
| Sodium Lauryl Sarcocinate | 0.5% | 1% |
| 2-mercaptoethanol | — | 150 mM |

Figure 3:
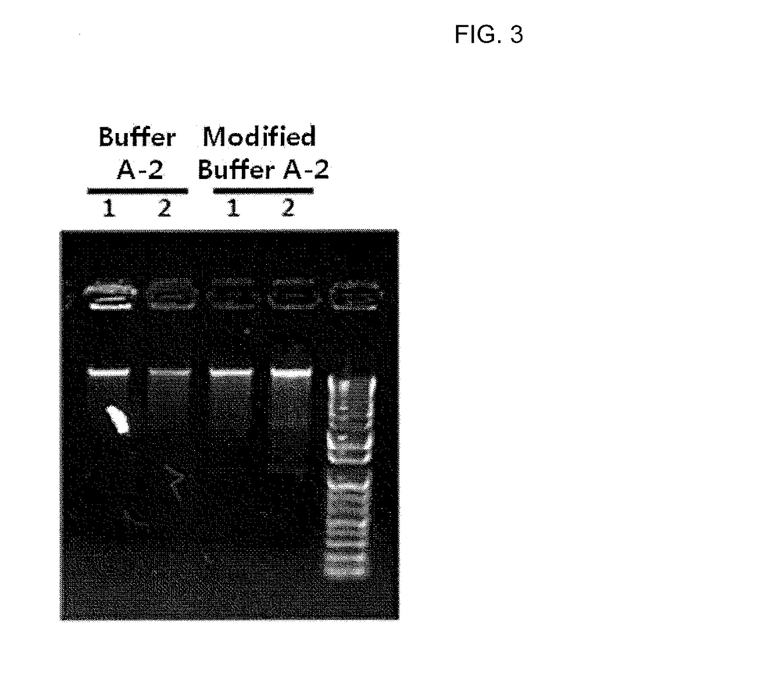
FIG. 3 shows electrophoresis results on whether or not all nucleic acids are isolated by using a modified cell lysis buffer according to the present invention.

It can be confirmed from FIG. 3 that, both of DNA and RNA were isolated in the modified cell lysis buffer (Modified Buffer A-2), but only DNA was isolated in the cell lysis buffer (Buffer A-2) of Example 2, not containing 2-mercaptoethanol.

Base on the above results, all of the nucleic acids were isolated through paper chromatography at a high speed by modifying the method of Example 2 using the modified cell lysis buffer (Modified Buffer A-2). It was confirmed that, when first and second mobile phase buffers were developed, some impurities were not removed from a portion of the silica membrane, which has been immersed in the cell lysate during the nucleic acid isolation procedure of Example 2.

Figure 7:
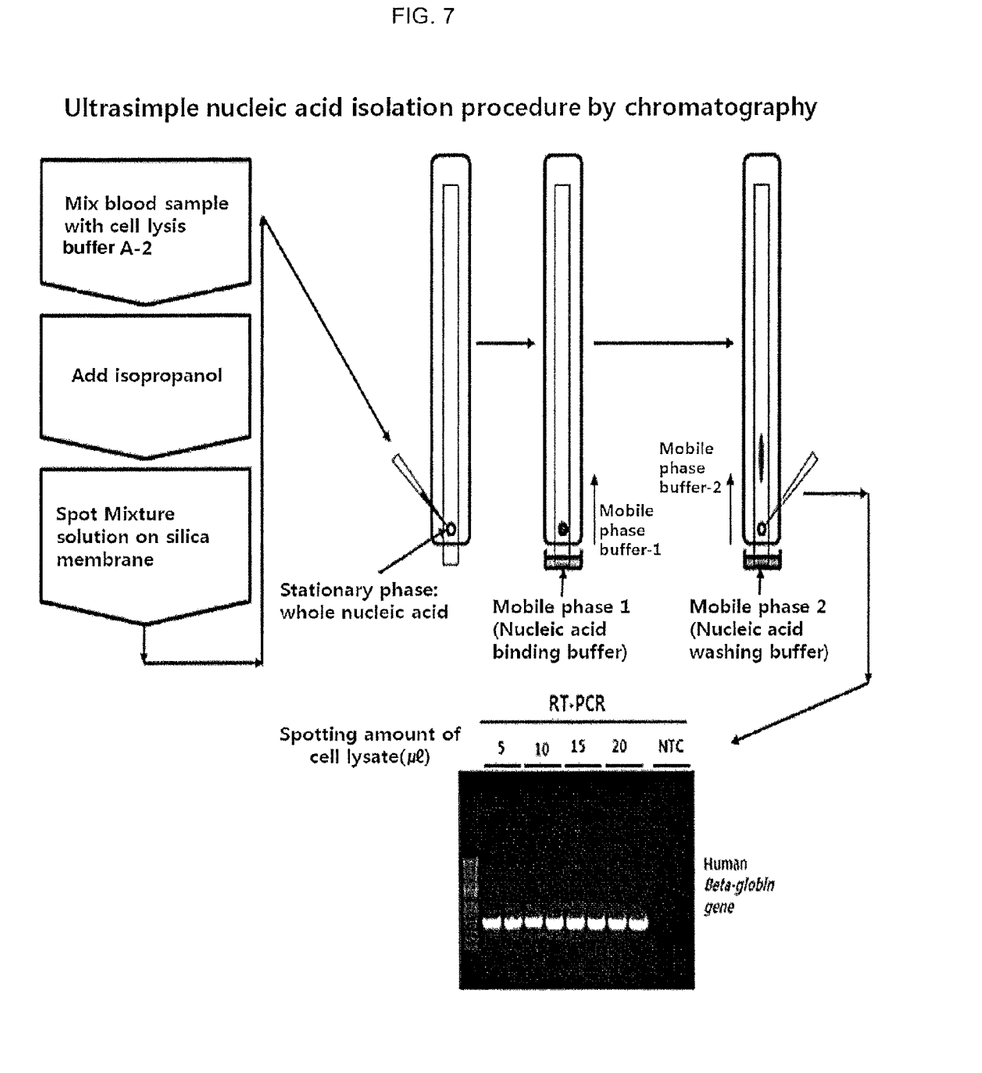
FIG. 7 shows a diagram for the method of rapid nucleic acid purification according to the present invention and a schematic view for the analyzing method thereof.

In the present test, in order to overcome this problem, as shown in FIG. 7, the cell lysate was spotted on a portion of a silica membrane (0.5 cm wide and 10 cm long), which is 1 cm above from a bottom edge of the silica membrane, and then the silica membrane was immersed only up to 0.5 cm from a bottom edge thereof in the mobile phase buffer, so that development of the mobile phase buffer was performed to effectively remove impurities from the cell lysate-spotted portion of the silica membrane. The remaining nucleic acid procedure was performed in the same manner as Example 2.

The above results showed that, in the rapid nucleic acid isolation and purification of Example 2 using the modified cell lysis buffer (Modified Buffer A-2) of the present invention, all the nucleic acids were efficiently isolated and also the target RNA was also confirmed.

(2) RT-PCR Detection of Target RNA from all of the Nucleic Acids

It was confirmed whether or not the target DNA is detectable from all of the nucleic acids isolated while being bound onto the silica membrane by the method (1) of Example 3, through RT-PCR.

To achieve this, a 2 mm-diameter portion was taken from a portion of the silica membrane onto which all the nucleic acids are bound, which has been isolated by the method of (1) of Example 3 while being bound onto the silica membrane, and then the RT-PCR detection reaction of the target RNA was performed by using a primer set designed from a transcript sequence for a human beta-globin gene, each 10 pmoles of a forward primer 5'-CAAGGTGAACGTGGATGAAG-3' (SEQ ID NO: 3) and a reverse primer 5'-GGCAGAATCCA-GATGCTCAA-3'(SEQ ID NO: 4); and a reaction buffer containing 1.25 units of HELIXAMP™ Hot-Taq DNA polymerase (Nanohelix, Korea), 25 units of HELIXCRIPT™ Thermo Reverse transcriptase (Nanohelix, Korea), a final concentration 2.5 mM of $MgCl_2$, and 0.25 mM of dNTP mix. The RT-PCR was performed under the conditions of 50° C. (40 minutes), 1 cycle / 95° C. (15 minutes), 1 cycle / 95° C. (20 seconds)- 55° C. (40 seconds) - 72° C. (1 minute), 35 cycles.

Figure 4:
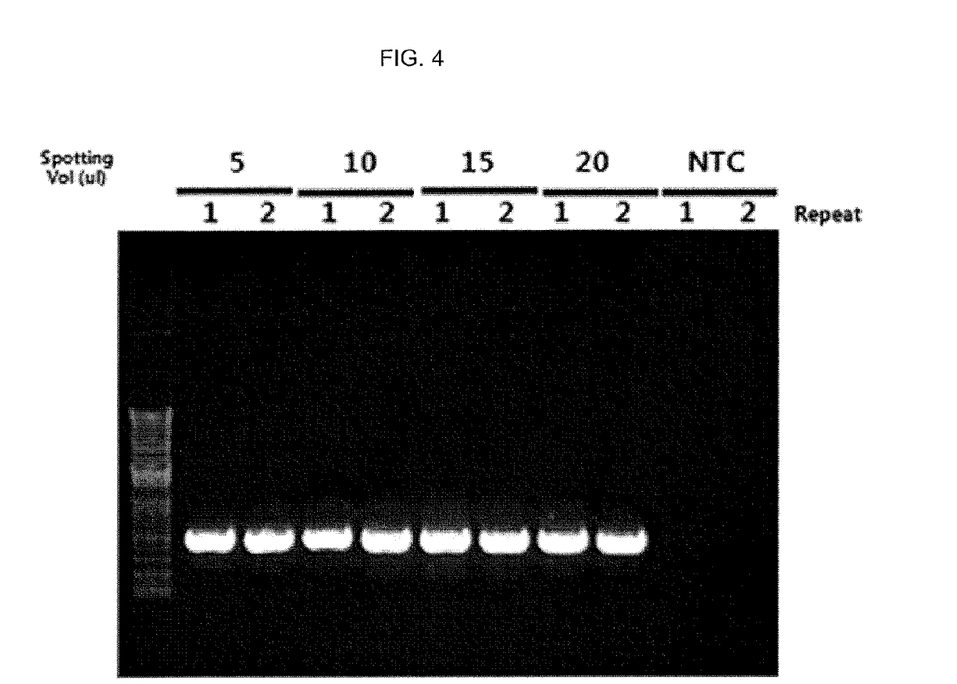
FIG. 4 shows RT-PCR analysis results on a target gene from DNA isolated by the method for rapid nucleic acid purification according to the present invention.

As seen from FIG. 4, as the RT-PCR results, 400 bp-sized beta globin RNA transcript was detected from the silica membrane onto which all the nucleic acids have been bound, and the target RNA was also detected even in the silica membrane where only 5 μl of the entire cell lysate has been spotted.

The results confirmed that the nucleic acid can be more conveniently and rapidly isolated from even a small amount of sample even without using special equipment, in the method of rapid nucleic acid isolation of the present invention, as compared with the nucleic acid isolation method of the related art.

(3) Verification on Real-Time PCR Amplification of Total Nucleic Acids

In the recent molecular diagnosis, real-time RT-PCR together with PCR and RT-PCR are used in detecting target DNA or RNA.

In the present invention, it was tested that the target DNA is detectable from the nucleic acid, which has been isolated by paper chromatography and bound onto the silica membrane, through real-time RT-PCR. To achieve this, a 2 mm-diameter portion was taken from a portion of total nucleic acids of the silica membrane, which has been isolated by the method of (1) of Example 3 while being bound onto the silica membrane, and then the real-time RT-PCR detection reaction thereof was performed by using a primer set designed from a transcript sequence for a human beta-globin gene, a forward primer 5'-CAAGGTGAACGTGGATGAAG-3' (SEQ ID NO: 5) and a reverse primer 5'-ATTAGCCACACCAGC-CACCAC-3'(SEQ ID NO: 6).

The real-time RT-PCR was performed under the conditions of 50° C. (40 minutes), 1 cycle / 95° C. (15 minutes), 1 cycle / 95° C. (20 seconds)-55° C. (40 seconds)- 72° C. (1 minutes), 35 cycles, by using a reaction buffer containing 25 units of HELIXCRIPT™ Thermo Reverse Transcriptase and 1.25 units of HELIXAMP™ Hot-Taq DNA polymerase, 0.25 mM of dNTP mix, and SYBR™ Green fluorescent agent; and each 10 pmoles of primer designed from a transcript sequence for a beta-globin gene.

It was analyzed whether or not the target DNA is amplified in real-time, by using Rotor-Spin type Qiagen ROTOR- GENE™ and Thermo Block type ABI7900HT real-time quantitative PCR analyzers, using the SYBR™ Green fluorescent agent.

Figure 5:
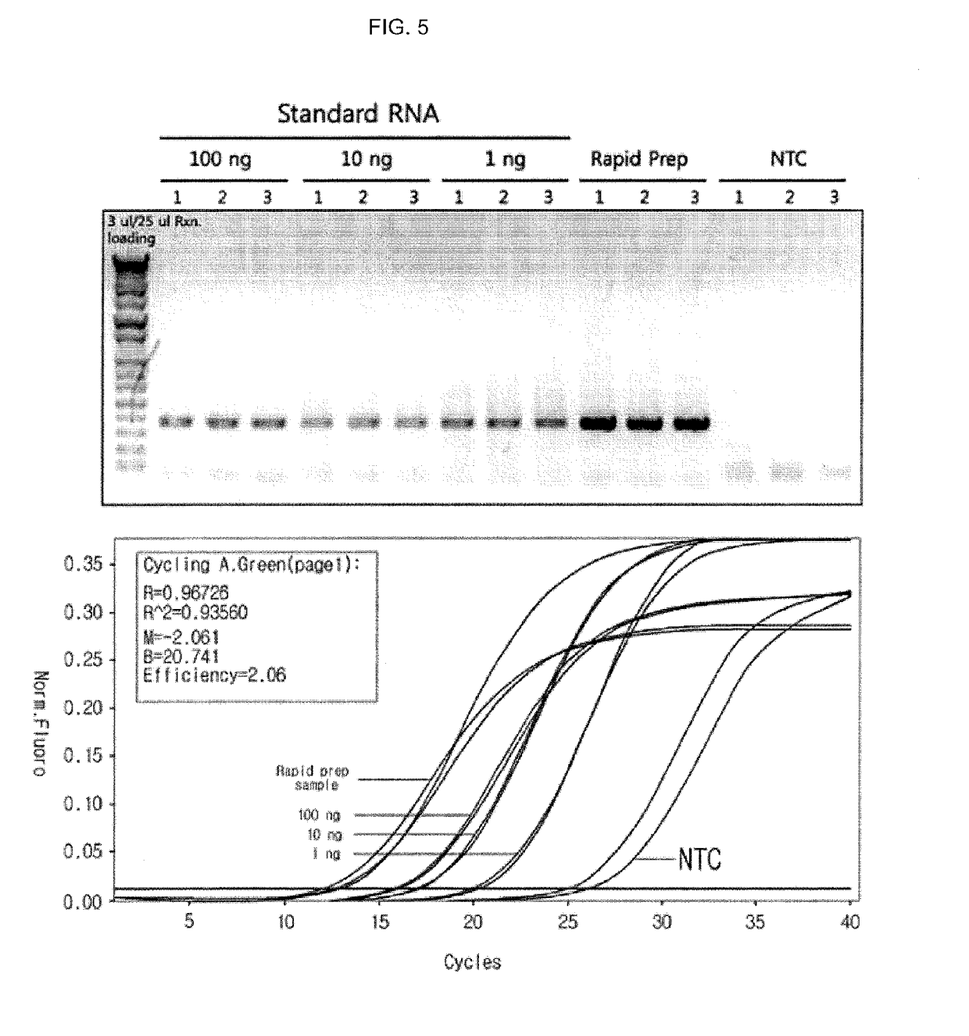
FIG. 5 shows analysis results on a target RNA from all nucleic acids isolated by the method for rapid nucleic acid purification according to the present invention, by using a Rotor-Spin type Qiagen ROTORGENE™ Q real-time quantitative PCR analyzer
Figure 6:
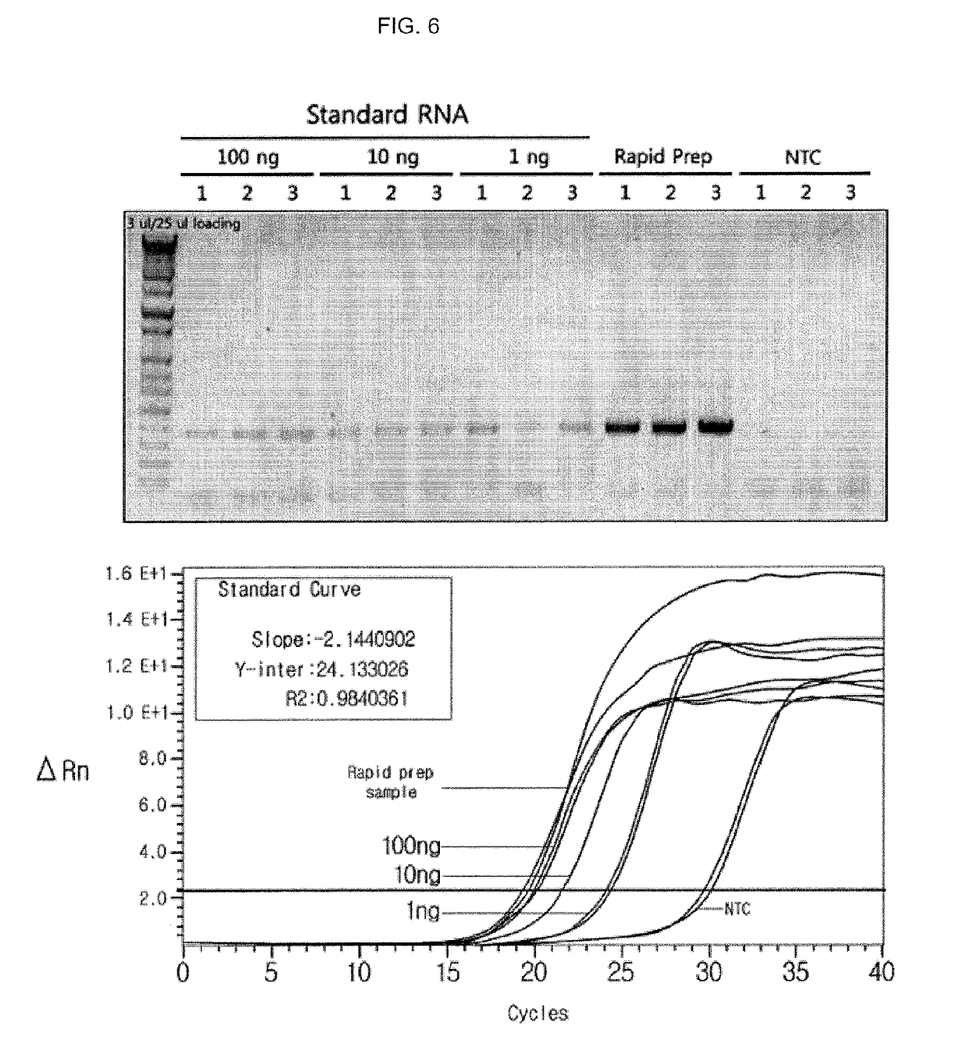
FIG. 6 shows analysis results on a target RNA from all nucleic acids isolated by the method for rapid nucleic acid purification according to the present invention, by using a Thermo Block type ABI7900HT real-time quantitative PCR analyzer.

As can be confirmed in FIGS. 5 and 6, as the results of real-time RT-PCR, a 350 bp-sized beta globin RNA transcript could be detected from the silica membrane onto which total the nucleic acids have been bound, and the nucleic acids isolated by the method for rapid nucleic acid isolation according to the present invention could be analyzed in both of the two types of real-time quantitative PCR analyzers.

As set forth above, the method for rapid nucleic acid isolation according to the present invention is very useful in diagnosing causes of disease or detecting a target gene; can be used in molecular diagnosis of causes of disease more rapidly and conveniently, as compared with the existing nucleic acid isolation method requiring complicated and special equipment; and can be used as an optimum nucleic acid isolation method for point-of-care testing (POCT).

Further, the method for rapid nucleic acid isolation according to the present invention does not require skills therefor, and thus, allows an ordinary person to personally conduct isolation of nucleic acid for analyzing causes of disease, so that it is possible to isolate nucleic acid even without going to the hospitals or health clinical centers, thereby removing the existing inconvenience.

What is claimed is:

1. A method for rapid nucleic acid purification, wherein a nucleic acid is isolated from a biological sample, the method comprising the following steps in order:
   1) obtaining a cell lysate by mixing the biological sample with a cell lysis buffer comprising a chaotropic salt and a sarcosinate, said cell lysate including a nucleic acid originated from the biological sample, and immersing a silica membrane into the cell lysate so that the nucleic acid is adsorbed on the silica membrane;
   2) immersing the silica membrane of step 1) into a mobile phase buffer for a sufficient time for the nucleic acid to migrate on the silica membrane; and
   3) immersing the silica membrane of step 2) into a nucleic acid washing buffer to elute the nucleic acid or performing at least one technique selected from PCR, RT-PCR, real-time PCR, and real-time RT-PCR directly on the nucleic acid bound onto the silica membrane.

2. The method of claim 1, wherein the lysis buffer further comprises guanidine thiocyanate.

3. The method of claim 1, wherein the mobile phase buffer comprises guanidine thiocyanate.

* * * * *